US009952149B2

(12) United States Patent
Superfine et al.

(10) Patent No.: US 9,952,149 B2
(45) Date of Patent: Apr. 24, 2018

(54) METHODS, SYSTEMS, AND COMPUTER READABLE MEDIA FOR DETERMINING PHYSICAL PROPERTIES OF A SPECIMEN IN A PORTABLE POINT OF CARE DIAGNOSTIC DEVICE

(71) Applicant: The University of North Carolina at Chapel Hill, Chapel Hill, NC (US)

(72) Inventors: Richard Superfine, Chapel Hill, NC (US); Bruce J. Oberhardt, Raleigh, NC (US); Richard Chasen Spero, Chapel Hill, NC (US); Michael Richard Falvo, Durham, NC (US); Briana Lee Fiser, High Point, NC (US); Russell Morton Taylor, II, Pittsboro, NC (US); Robert Michael Judith, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 143 days.

(21) Appl. No.: 14/648,845

(22) PCT Filed: Dec. 2, 2013

(86) PCT No.: PCT/US2013/072606
§ 371 (c)(1),
(2) Date: Jun. 1, 2015

(87) PCT Pub. No.: WO2014/085804
PCT Pub. Date: Jun. 5, 2014

(65) Prior Publication Data
US 2015/0300953 A1 Oct. 22, 2015

Related U.S. Application Data

(60) Provisional application No. 61/732,278, filed on Nov. 30, 2012.

(51) Int. Cl.
*G01N 33/86* (2006.01)
*G01N 33/49* (2006.01)
(Continued)

(52) U.S. Cl.
CPC ............. *G01N 21/47* (2013.01); *G01N 21/59* (2013.01); *G01N 33/49* (2013.01); *G01N 21/82* (2013.01);
(Continued)

(58) Field of Classification Search
CPC .. G01N 2021/825; G01N 21/47; G01N 21/59; G01N 2201/02; G01N 2201/062;
(Continued)

(56) References Cited

U.S. PATENT DOCUMENTS 4,408,277 A 10/1983 Cortellini et al.
4,462,096 A 7/1984 Kusaka
(Continued)

FOREIGN PATENT DOCUMENTS

EP 1016460 A2 7/2000
JP 5511949 4/2014
(Continued)

OTHER PUBLICATIONS

Non-Final Office Action for U.S. Appl. No. 14/016,007 (dated May 18, 2015).
(Continued)

*Primary Examiner* — Maureen Wallenhorst
(74) *Attorney, Agent, or Firm* — Jenkins, Wilson, Taylor & Hunt, P.A.

(57) ABSTRACT

Methods, systems, and computer readable media for determining physical properties of a specimen in a portable point of care device are disclosed. According to one aspect, a method includes placing a specimen onto an active surface that includes a plurality of microposts extending outwards
(Continued)

from a substrate, wherein each micropost includes a proximal end attached to the substrate and a distal end opposite the proximal end and generating an actuation force in proximity to the micropost array that compels at least some of the microposts to exhibit motion. The method further includes detecting light that is emitted by an illumination source and interacts with the active surface while the at least some microposts exhibit motion in response to the actuation force, measuring data that represents the detected light interacting with the active surface, and determining at least one physical property of the specimen based on the measured data.

12 Claims, 4 Drawing Sheets

(51) Int. Cl.
  *G01N 33/483* (2006.01)
  *G01N 21/47* (2006.01)
  *G01N 21/59* (2006.01)
  *G01N 21/17* (2006.01)
  G01N 21/82 (2006.01)
  G01N 27/22 (2006.01)
  G01N 27/72 (2006.01)

(52) U.S. Cl.
  CPC ............ *G01N 27/22* (2013.01); *G01N 27/72* (2013.01); *G01N 33/4905* (2013.01); *G01N 2021/825* (2013.01); *G01N 2201/02* (2013.01); *G01N 2201/062* (2013.01)

(58) Field of Classification Search
  CPC ........ G01N 27/22; G01N 27/72; G01N 33/49; G01N 33/4905; G01N 21/6456; G01N 21/82
  USPC ............ 436/63, 69, 73, 149, 151, 164, 165; 422/73, 82.01, 82.05, 82.09; 435/13; 506/12, 13
  See application file for complete search history.

(56) References Cited

U.S. PATENT DOCUMENTS

| | | | |
|---|---|---|---|
| 4,849,340 A | 7/1989 | Oberhardt |
| 5,110,727 A | 5/1992 | Oberhardt |
| 5,206,504 A | 4/1993 | Sridharan |
| 5,350,676 A | 9/1994 | Oberhardt et al. |
| 5,410,370 A | 4/1995 | Janssen |
| 5,436,448 A | 7/1995 | Hosaka et al. |
| 5,458,785 A | 10/1995 | Howe et al. |
| 5,467,146 A | 11/1995 | Huang et al. |
| 5,483,058 A | 1/1996 | Leviton |
| 5,528,318 A | 6/1996 | Janssen |
| 5,548,058 A | 8/1996 | Muroi et al. |
| 5,627,037 A | 5/1997 | Ward et al. |
| 5,638,303 A | 6/1997 | Edberg et al. |
| 5,668,611 A | 9/1997 | Ernstoff et al. |
| 5,698,843 A | 12/1997 | Phak |
| 5,777,215 A | 7/1998 | Calatzis et al. |
| 5,903,323 A | 5/1999 | Ernstoff et al. |
| 5,976,369 A | 11/1999 | Howe et al. |
| 6,018,402 A | 1/2000 | Campbell et al. |
| 6,067,207 A | 5/2000 | Kurita |
| 6,162,364 A | 12/2000 | Tillotson et al. |
| 6,219,110 B1 | 4/2001 | Ishikawa et al. |
| 6,269,324 B1 | 7/2001 | Rakijas et al. |
| 6,330,824 B1 | 12/2001 | Erie et al. |
| 6,370,107 B1 | 4/2002 | Hosaka et al. |
| 6,412,429 B2 | 7/2002 | Foresman |
| 6,412,972 B1 | 7/2002 | Pujol et al. |
| 6,428,169 B1 | 8/2002 | Deter et al. |
| 6,442,416 B1 | 8/2002 | Schultz |
| 6,456,339 B1 | 9/2002 | Surati et al. |
| 6,457,833 B1 | 10/2002 | Ishikawa et al. |
| 6,470,226 B1 | 10/2002 | Olesen et al. |
| 6,493,149 B2 | 12/2002 | Ouchi |
| 6,496,332 B1 | 12/2002 | Okazaki et al. |
| 6,503,195 B1 | 1/2003 | Keller et al. |
| 6,545,580 B2 | 4/2003 | Hegde et al. |
| 6,549,004 B1 | 4/2003 | Prigge |
| 6,588,944 B2 | 7/2003 | Harris |
| 6,596,076 B1 | 7/2003 | Wakayama |
| 6,609,798 B1 | 8/2003 | Milinusic et al. |
| 6,624,919 B2 | 9/2003 | Lambert |
| 6,636,275 B1 | 10/2003 | Wilson |
| 6,650,213 B1 | 11/2003 | Sakurai et al. |
| 6,716,642 B1 | 4/2004 | Wu et al. |
| 6,769,792 B1 | 8/2004 | Bornhorst |
| 6,794,197 B1 | 9/2004 | Indermuhle et al. |
| 6,881,954 B1 | 4/2005 | Morimoto et al. |
| 6,885,266 B2 | 4/2005 | Ochi-Okorie |
| 6,936,471 B2 | 8/2005 | Hajduk et al. |
| 6,958,816 B1 | 10/2005 | Dogariu et al. |
| 7,119,645 B2 | 10/2006 | Vicci et al. |
| 7,189,969 B2 | 3/2007 | Vicci et al. |
| 7,191,092 B2 | 3/2007 | Vicci et al. |
| 7,305,319 B2 | 12/2007 | Vicci et al. |
| 8,152,305 B2 | 4/2012 | Keller et al. |
| 8,490,469 B2 | 7/2013 | Superfine et al. |
| 8,586,368 B2 | 11/2013 | Superfine et al. |
| 9,213,024 B2 * | 12/2015 | Sniadecki .......... G01N 33/5302 |
| 9,612,185 B2 | 4/2017 | Superfine et al. |
| 2001/0055462 A1 | 12/2001 | Seibel |
| 2002/0008812 A1 | 1/2002 | Conner et al. |
| 2002/0171809 A1 | 11/2002 | Kurtz et al. |
| 2002/0176149 A1 | 11/2002 | Davis et al. |
| 2003/0004985 A1 | 1/2003 | Kagimasa et al. |
| 2003/0013079 A1 | 1/2003 | Petropoulos |
| 2003/0024911 A1 | 2/2003 | Horsting et al. |
| 2003/0118222 A1 | 6/2003 | Foran et al. |
| 2003/0203271 A1 | 10/2003 | Morse et al. |
| 2003/0227465 A1 | 12/2003 | Morgan et al. |
| 2004/0140981 A1 | 7/2004 | Clark |
| 2004/0141213 A1 | 7/2004 | Kleiman |
| 2004/0191915 A1 | 9/2004 | Bawendi et al. |
| 2004/0241759 A1 | 12/2004 | Tozer et al. |
| 2004/0244470 A1 | 12/2004 | Vicci et al. |
| 2004/0262210 A1 | 12/2004 | Westervelt et al. |
| 2005/0015001 A1 | 1/2005 | Lec et al. |
| 2005/0064395 A1 | 3/2005 | Israel et al. |
| 2005/0231651 A1 | 10/2005 | Myers et al. |
| 2005/0276727 A1 | 12/2005 | Pawliszyn et al. |
| 2006/0068107 A1 | 3/2006 | Madou et al. |
| 2006/0219904 A1 | 10/2006 | Vicci et al. |
| 2006/0229842 A1 | 10/2006 | Vicci et al. |
| 2007/0031819 A1 | 2/2007 | Koschwanez et al. |
| 2008/0257754 A1 * | 10/2008 | Pugia ................ B01L 3/502723 205/792 |
| 2008/0261261 A1 | 10/2008 | Grimes et al. |
| 2009/0009723 A1 | 1/2009 | Keller et al. |
| 2009/0220561 A1 | 9/2009 | Jin et al. |
| 2009/0253215 A1 | 10/2009 | Hikmet et al. |
| 2010/0101308 A1 | 4/2010 | Superfine et al. |
| 2011/0003710 A1 | 1/2011 | Konstantopoulos et al. |
| 2011/0151491 A1 | 6/2011 | Dennis et al. |
| 2011/0240476 A1 | 10/2011 | Wang et al. |
| 2012/0028818 A1 | 2/2012 | Öhman et al. |
| 2012/0107851 A1 | 5/2012 | Killard et al. |
| 2012/0156791 A1 | 6/2012 | Superfine et al. |
| 2014/0001146 A1 | 1/2014 | Superfine et al. |

FOREIGN PATENT DOCUMENTS

| | | |
|---|---|---|
| WO | WO 02/093738 A2 | 11/2002 |
| WO | WO 03/029921 | 4/2003 |
| WO | WO 2006/020187 A2 | 2/2006 |
| WO | WO 2008/103430 A2 | 8/2008 |
| WO | WO 2008/139401 A2 | 11/2008 |

(56) References Cited

FOREIGN PATENT DOCUMENTS

| | | |
|---|---|---|
| WO | WO 2010/151780 A2 | 12/2010 |
| WO | WO 2012/079076 A2 | 6/2012 |

OTHER PUBLICATIONS

Thromboelastography, Wikipedia, http://en.wikipedia.org/wiki/Thromboelastography, pp. 1-3 (Apr. 22, 2015).
Extended European Search Report for European Application No. 10792732.9 (dated Mar. 3, 2015).
Notification of Transmittal of the International Search Report and the Written Opinion of the International Searching Authority, or the Declaration for International Application No. PCT/US2013/072606 (dated Mar. 21, 2014).
Notice of Allowance and Fee(s) Due for U.S. Appl. No. 13/380,564 (dated Jul. 12, 2013).
Restriction and/or Election Requirement for U.S. Appl. No. 13/380,564 (dated May 24, 2013).
Supplemental Notice of Allowability for U.S. Appl. No. 12/528,312 (dated Apr. 25, 2013).
Notice of Allowance and Fee(s) Due for U.S. Appl. No. 12/528,312 (dated Mar. 21, 2013).
Notification of Transmittal of the International Search Report and the Written Opinion of the International Searching Authority, or the Declaration for International Application No. PCT/US2011/064412 (dated Sep. 26, 2012).
Non-Final Official Action for U.S. Appl. No. 12/528,312 (dated Jun. 19, 2012).
Communication of European publication number and information on the application of Article 67(3) EPC for European Application No. 10792732.9 (dated Apr. 4, 2012).
Notice of Allowance and Fee(s) Due for U.S. Appl. No. 11/632,151 (dated Dec. 23, 2011).
Final Official Action for U.S. Appl. No. 11/632,151 (dated Jul. 28, 2011).
Commonly-assigned, co-pending U.S. Appl. No. 61/491,627 for "Method for Permeability Measurement of Blood, Plasma, or Fibrin Clots and Other Polymer Gels," (Unpublished, filed May 31, 2011).
Interview Summary for U.S. Appl. No. 11/632,151 (dated Mar. 29, 2011).
Notification of Transmittal of the International Search Report and the Written Opinion of the International Searching Authority, or the Declaration for International Application No. PCT/US2010/040011 (dated Feb. 15, 2011).
Non-Final Office Action for U.S. Appl. No. 11/632,151 (dated Feb. 9, 2011).
Shields et al., "Biomimetic cilia arrays generate simultaneous pumping and mixing regimes," Proceedings of the National Academy of Sciences, vol. 107, No. 36, pp. 15670-15475 (Sep. 7, 2010).
MacDonald et al., "Critical Factors Contributing to the Thromboelastography Trace," Seminars in Thrombosis and Hemostasis, vol. 36, No. 7, pp. 712-722 (2010).
Johansson et al., "Thrombelastography and tromboelastometry in assessing coagulopathy in trauma," Scandinavian Journal of Trauma, Resuscitation and Emergency Medicine, vol. 17, pp. 1-8 (2009).
Notification of Transmittal of the International Search Report and the Written Opinion of the International Searching Authority, or the Declaration for International Application No. PCT/US08/02331 (dated Jun. 25, 2008).
Sniadecki et al., "Magnetic microposts for mechanical stimulation of biological cells: Fabrication, characterization, and analysis," Review of Scientific Instruments, vol. 79, No. 4, pp. 044302-1-044302-8 (Apr. 16, 2008).
Belmiloud et al., "Rheological Behavior Probed by Vibrating Microcantilevers," Applied Physics Letters, vol. 92, pp. 041907-041907-3 (Jan. 30, 2008).
Groβe et al., "Dynamic calibration technique for the micro-pillar shear-stress sensor MPS3," Measurement Science & Technology, vol. 19, No. 10, pp. 1-12 (2008).
Martini et al., "Thrombelastography is Better Than PT, aPTT, and Activated Clotting Time in Detecting Clinically Relevant Clotting Abnormalities After Hypothermia, Hemorrhagic Shock and Resuscitation in Pigs," The Journal of TRAUMA, Injury, Infection & Critical Care, vol. 65, No. 3, pp. 535-543 (2008).
Sniadecki et al., "Magnetic Microposts as an Approach to Apply Forces to Living Cells," Proceedings of Natual Academy of Sciences, vol. 104, No. 37 (Sep. 11, 2007).
Notice of Allowance and Fee(s) Due for U.S. Appl. No. 10/487,860 (dated Jul. 25, 2007).
Evans et al., "Magnetically Actuated Nanorod Arrays as Biomimetic Cilia," American Chemical Society, vol. 7, No. 5, pp. 1428-1434 (Apr. 10, 2007).
Non-Final Office Action for U.S. Appl. No. 10/487,860 (dated Feb. 28, 2007).
Commonly-assigned, co-pending U.S. Appl. No. 60/901,943 for "Agnostic Tracking," (Unpublished, filed Feb. 16, 2007).
Supplemental Notice of Allowability for U.S. Appl. No. 11/440,912 (dated Feb. 7, 2007).
Supplemental Notice of Allowability for U.S. Appl. No. 11/440,881 (dated Feb. 7, 2007).
Interview Summary for U.S. Appl. No. 10/487,860 (dated Jan. 22, 2007).
Brucker et al., "Dynamic response of micro-pillar sensors measuring fluctuating wall-shear-stress," Experiments in Fluids, vol. 42, No. 5, pp. 737-749 (2007).
Brohi et al., "Acute coagulopathy of trauma: mechanism, identification and effect," Current Opinion in Critical Care, vol. 13, pp. 680-685 (2007).
Kauvar et al., "Impact of Hemorrhage on Trauma Outcome: An overview of Epidemiology, Clinical Presentations, and Therapeutic Considerations," The Journal of Trauma, vol. 60, No. 6, pp. S3-S11 (2006).
Yun et al., "Carbon Nanotube Array Smart Materials," SPIE, vol. 6172, pp. 617205-1-617205-12 (Dec. 31, 2006).
Notification of Transmittal of the International Search Report and the Written Opinion of the International Searching Authority, or the Declaration for International Application No. PCT/US05/25380 (dated Oct. 26, 2006).
Supplemental Notice of Allowability for U.S. Appl. No. 10/786,427 (dated Aug. 17, 2006).
Notice of Allowance and Fee(s) Due for U.S. Appl. No. 11/440,912 (dated Jul. 25, 2006).
Notice of Allowance and Fee(s) Due for U.S. Appl. No. 11/440,881 (dated Jul. 25, 2006).
Final Official Action for U.S. Appl. No. 10/487,860 (dated Jul. 19, 2006).
Notice of Allowance and Fee(s) Due for U.S. Appl. No. 10/786,427 (dated Mar. 28, 2006).
3rdTech, "HiBall™-3100 Wide-Area Tracker and 3D Digitizer," 3rd Tech, Inc. (2006).
Groβe et al., "Nano-newton drag sensor based on flexible micropillars," Measurement Science and Technology, vol. 17, pp. 2689-2697 (2006).
Spahn et al., "Coagulopathy and blood component transfusion in trauma," British Journal of Anaesthesia, vol. 95, No. 2, pp. 130-139, (2005).
Kauvar et al., "The epidemiology and modern management of traumatic hemorrhage: US and international persectives," Critical Care, vol. 9, Suppl. 5, pp. S1-S9 (2005).
Non-Final Office Action in U.S. Appl. No. 10/487,860 (dated Dec. 7, 2005).
Restriction Requirement for U.S. Appl. No. 10/786,427 (dated Oct. 4, 2005).
Notification of Transmittal of International Preliminary Examination Report for International Application No. PCT/US02/30853 (dated Mar. 4, 2004).
Brohi et al., "Acute Traumatic Coagulopathy," The Journal of TRAUMA, Injury, Infection, and Critical Care. vol. 54, No. 6, pp. 1127-1130 (Jun. 2003).

(56) References Cited

OTHER PUBLICATIONS

Notification of Transmittal of the International Search Report or the Declaration for International Application No. PCT/US02/30853 (dated May 7, 2003).
Prisco et al., "Point-of-Care Testing of Hemostasis in Cardiac Surgery," Thrombosis Journal, vol. 1, No. 1, 10 pgs. (May 2003).
Jian Ling, "Toward Raman Spectroscopy of Biological Tissue for Cancer Diagnosis", Southwest Research Institue IR&D, 10-9359 (Feb. 2003).
Roth et al., "Wide Gamut, High Brightness Multiple Primaries Single Panel Projection Displays," SID Digest, ISSN/0003-0966X/03/3403-0694 (Copyright 2003).
Peden et al., "The Injury Chart Book: A grahical overview of the global burden of injuries," Geneva, World Health Organization, pp. 1-81 (2002).
Wilde, "Three-Dimensional Force Microscope," (Downloaded from the Internet on Jun. 24, 2002).
"MFP-3D™ Atomic Force Microscope Power and Flexibility in One Complete System" Asylum Research, pp. 1-4 (Jun. 5, 2002).
Lee et al., "Microelectromagnets for the Control of Magnetic Nanoparticles," Applied Physics Letters, vol. 79, No. 20, pp. 3308-3310 (Nov. 12, 2001).
Vicci, "A 3D Magnetic Force Manipulator DC Prototype," Department of Computer Science, UNC Chapel Hill (Oct. 17, 2001).
Requicha et al., "Manipulation of Nanoscale Components with the AFM: Principles and Applications," Proceedings of the 2001 1st IEEE Conference on Nanotechnology, pp. 81-86 (Oct. 2001).
Baldis, "Institute for Laser Science and Applications," U.S. Department of Energy, UCRL-ID-145269, pp. 53-55 (Aug. 27, 2001).
Vicci, "A 3D Magnetic Force Manipulator DC Prototype," Department of Computer Science, UNC Chapel Hill (Jul. 3, 2001).
Heaton et al., "Scanning Probe/Atomic Force Microscopy: Technology Overview and Update," pp. 1-8 (Mar. 2001).
Welch et al., "High-Performance Wide-Area Optical Tracking—The HiBall Tracking System," Presence, vol. 10, No. 1, Massachusetts Institute of Technology (Feb. 2001).
Choi et al., "An On-Chip Magnetic Bead Separator Using Spiral Electromagnets with Semi-Encapsulated Permalloy," Biosensors & Bioelectronics 16, pp. 409-416 (2001).
"Atomic Force Microscopy," Veeco Metrology Group (Downloaded from the Internet on Jun. 24, 2002) (Copyright 2001).
Ahmed et al., "Measurement of solution viscosity by atomic force microscopy," Review of Scientific Instruments, vol. 72, No. 6, pp. 2731-2734 (2001).
Keller et al., "Real-time Structured Light Depth Extraction," Three Dimensional Image Capture and Applications III; SPIE Proceedings, p. 11-18; Photonics West—Electronic Imaging 2000 (Jan. 2000).
Choi et al., "A New Magnetic Bead-Based, Filterless Bio-Separator with Planar Electromagnet Surfaces for Integrated Bio-Detection Systems," Sensors and Actuators B 68, pp. 34-39 (2000).
Stavros Demos, "Endoscopic Subsurface Optical Imaging for Cancer Detection," Institute for Laser Science and Applications Report 2000 (2000).
Welch et al., "The HiBall Tracker: High-Performance Wide-Area Tracking for Virtual and Augmented Environments," Symposium on Virtual Reality Software and Technology, University College London (Dec. 20-22, 1999).
Ajito et al., "Six-Primary Color Projection Display for Expanded Color Gamut Reproduction," International Symposium on Multispectral Imaging and Color Reproduction for Digital Archives, Chiba, Japan, pp. 135-138 (1999).
Lapcik, Jr. et al., "Hyaluronan: Preparation, Structure, Properties, and Applications," Chemical Reviews, vol. 98, No. 8, pp. 2663-2684 (1998).
Sader et al., "Frequency response of cantilever beams immersed in viscous fluids with applications to the atomic force microscope," Journal of Applied Physics, vol. 84, No. 1, pp. 64-76 (1998).
Ahn et al., "Micromachined Planar Inductors on Silicon Wafers for MEMS Applications," IEEE Transactions on Industrial Electronics, vol. 45, No. 6, pp. 866-876 (Dec. 1998).
Drndić et al., "Micro-Electromagnets for Atom Manipulation," Applied Physics Letters, vol. 72, No. 22, pp. 2906-2908 (Jun. 1, 1998).
Ahn et al., "A Fully Integrated Micromachined Magnetic Particle Separator," Journal of Microelectromechanical Systems, vol. 5, No. 3, pp. 151-158 (Sep. 1996).
Hosaka et al., "Damping Characteristics of Beam-Shaped Micro-Oscillators," Elsevier Science Sensors and Actuators, vol. 49, pp. 87-95 (Feb. 1995).
Ahn et al., "A Fully Integrated Planar Toroidal Inductor with a Micromachined Nickel-Iron Magnetic Bar," IEEE Transactions on Components, Packaging, and Manufacturing Technology—Part A, vol. 17, No. 3, pp. 463-469 (Sep. 1994).
Oberhardt et al., "Dry Reagent Technology for Rapid, Convenient Measurements of Blood Coagulation and Fibrinolysis," Clinical Chemistry, vol. 37, No. 4, pp. 520-526 (1991).
"The First Commercial Low Temperature Near-field Optical Microscope," NSOM/AFM 100 Confocal LT™, pp. 1-2 (Publication Date Unknown).
Communication of the Extended European Search Report for Euroopean Application No. 13858774.6 (dated Jun. 8, 2016).
Communication of European publication number and information on the application of Article 67(3) EPC for European Application No. 13858774.6 (dated Sep. 9, 2015).
Richard Lloydd Carroll and Richard Superfine, Slides from Presentations Relating to UNC Invention Disclosure No. 05-0112, Actuable, Magnetic Field Patterned Microstructures , pp. 1-5 (2005).

\* cited by examiner

METHODS, SYSTEMS, AND COMPUTER READABLE MEDIA FOR DETERMINING PHYSICAL PROPERTIES OF A SPECIMEN IN A PORTABLE POINT OF CARE DIAGNOSTIC DEVICE

PRIORITY CLAIM

This application claims the benefit of U.S. Provisional Patent Application Ser. No. 61/732,278 filed on Nov. 30, 2012, the disclosure of which is incorporated herein by reference in its entirety.

GOVERNMENT INTEREST

This invention was made with government support under Grant Nos. HL109791 and EB002025 awarded by the National Institutes of Health. The government has certain rights in the invention.

TECHNICAL FIELD

The subject matter described herein relates to methods and systems for measuring physical properties of specimens using surface-attached actuated microposts in a point of care diagnostic device. More particularly, the subject matter described herein relates to methods, systems, and computer readable media for determining physical properties of a specimen in a portable point of care diagnostic device.

BACKGROUND

The viscoelasticity of biofluids, such as blood clots or mucus, is critical to their performance. Measurement of viscoelastic and other physical properties of a patient's biofluids can provide important information to medical professionals and caretakers. For example, the speed and strength at which a blood clot forms provides valuable information that can aid in providing efficient and efficacious treatment to the patient. Prompt diagnosis and medical treatment are invaluable in light the large number of deaths caused annually by traumatic injuries.)

Physical properties of a biofluid, such blood clot elasticity, are typically measured either in an established clinical laboratory or at the point of care (POC). Notably, clot elasticity may be measured within an analytical lab setting using specialized techniques, such as thromboelastography (TEG), to determine the blood coagulation parameters. However, the TEG techniques use a macroscopic quantity of specimen and measure viscoelasticity by applying the specimen between two surfaces which are configured to move with respect to each other in shear (e.g., two concentric cylinders). Such tests are typically performed using desk/table top instruments that must be operated on level surfaces, thereby making it impractical to utilize the present techniques to measure biofluid properties outside of a laboratory setting, such as at the bedside or in the field, for example in the case of trauma patients. Unfortunately, a large majority of traumatic accidents occur outside of and far away from laboratory facilities, thereby rendering the current analytical equipment ineffective for use in trauma-related diagnosis to guide appropriate therapeutic intervention in a timely manner.

Accordingly, there exists a need for methods, systems, and computer readable media for determining physical properties of a specimen in a portable point of care diagnostic device.

SUMMARY

According to one aspect of the present subject matter, a method includes placing a specimen onto an active surface that comprises a plurality of microposts extending outwards from a substrate, wherein each micropost includes a proximal end attached to the substrate and a distal end opposite the proximal end and generating an actuation force in proximity to the micropost array that compels at least some of the microposts to exhibit motion. The method further includes detecting light that is emitted by an illumination source and interacts with the active surface while the at least some microposts exhibit motion in response to the actuation force, measuring data that represents the detected light interacting with the active surface, and determining at least one physical property of the specimen based on the measured data.

According to one aspect of the present subject matter, a system includes an active surface configured to receive a specimen and includes a plurality of microposts extending outwards from a substrate, wherein each micropost includes a proximal end attached to the substrate and a distal end opposite the proximal end. The system further includes an actuation unit configured to generate an actuation force in proximity to the micropost array that compels at least some of the microposts to exhibit motion and a detection unit configured to detect light that is emitted by an illumination source and interacts with the active surface while the at least some microposts exhibit motion in response to the actuation force. The system also includes a processing unit configured to measure data that represents the detected light interacting with the active surface and to determine at least one physical property of the specimen based on the measured data.

The subject matter described herein for determining physical properties of a specimen in a portable point of care diagnostic device may be implemented in hardware in combination with software and/or firmware. As such, the terms "function" or "module" as used herein refer to hardware, software, and/or firmware for implementing the feature being described. In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a non-transitory computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which.

DETAILED DESCRIPTION

Figure 1:
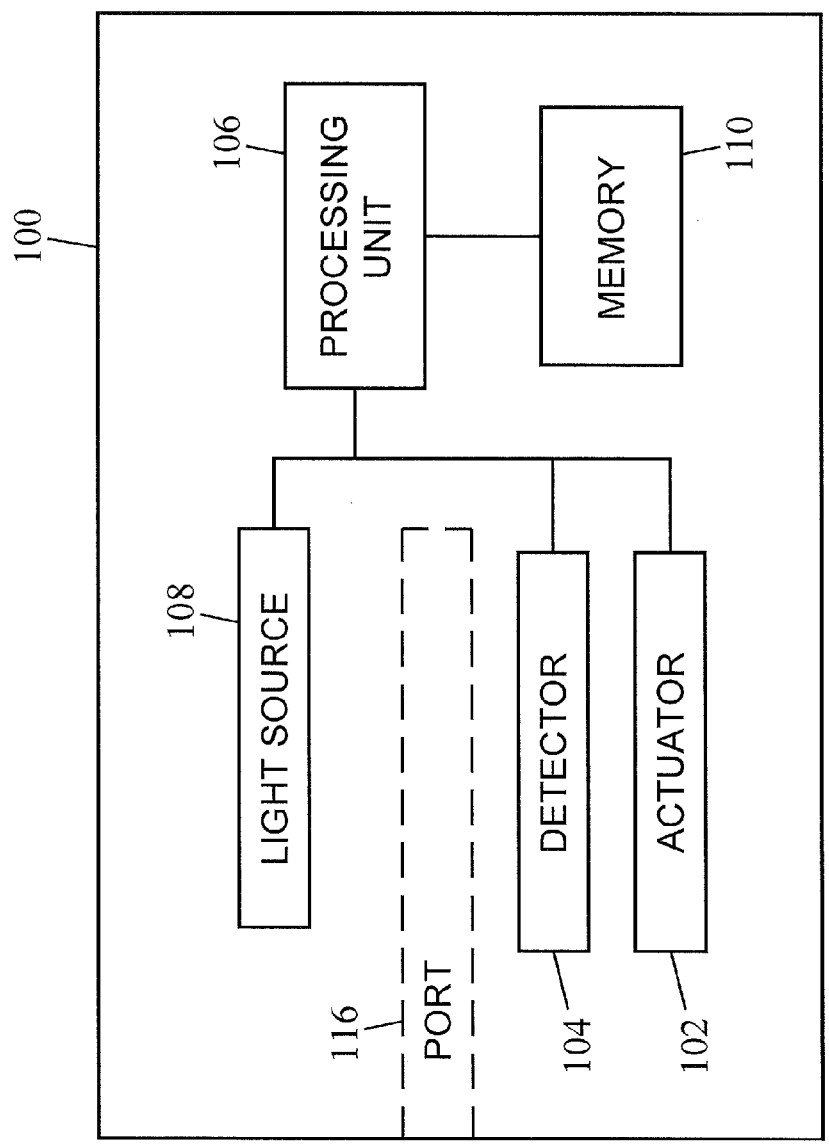
FIG. 1 is a block diagram depicting a profile view of a portable point of care diagnostic device for determining physical properties of a specimen according to an embodiment of the subject matter described herein.
Figure 1:
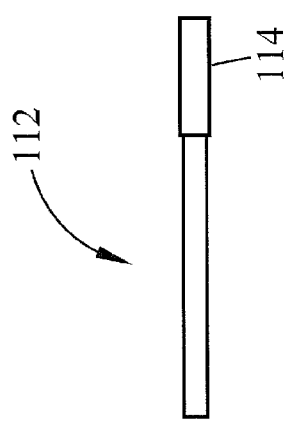

In accordance with the subject matter disclosed herein, systems, methods, and computer readable media are provided for determining physical properties of a specimen (e.g., an analyte) in a portable and/or hand-held point of care diagnostic device. The subject matter disclosed herein is directed to the application of an applied force, such as an electric or magnetic force, to an active surface. Although the following description provides specific examples of an active surface, the active surface may generally include any structure or group of structures that can be characterized as having i) a flexible portion, ii) a portion that responds to a drive signal (e.g., magnetic or electric signal), and iii) a portion that is responsive to detection. For example, an active surface may comprise a micropost array that includes flexible surface attached microposts, where the array is made up at least in part of an elastic material, such as an elastomer. In one embodiment, microposts may be described as surface attached posts (SAPs) that are anchored at one end to a base or substrate. For example, the microposts may include a plurality of approximately 25 micrometer tall polydimethylsiloxane (PDMS) pillars with diameters measuring approximately 2 micrometers. Alternate embodiments of microposts include various heights and diameters (all of which are typically measured in the scale of micrometers). In one embodiment, the surface attached microposts are attached to a (partially or entirely) transparent substrate. For example, the substrate may be a 500 micrometer thick glass wafer. The viscoelastic properties of a specimen may be measured by placing the specimen on such microposts (e.g., micrposts immersed by specimen), and applying an actuating force to the microposts. The subject matter may include measuring the movement, or change in movement over time, of the microposts. Alternatively, the subject matter may include measuring the amplitude of detected light that has interacted with actuated microposts constituting the active surface. Microposts of a micropost array may be located, for example, on a tab to be used with a point of care diagnostic device (i.e., "point of care device"). The point of care device may be embodied as a bench-top device, a handheld device, a mobile device, or a rugged device that is configured to function without the use of microscopy or magnification. Notably, the point of care device may be used at a point of care, near a patient, or in the field. Characteristics, attributes, or properties of the microposts may also be configurable in such a manner that allows for the calibration of an applied actuation force. For example, attributes of the microposts that may be configured include, but are not limited to, the diameter, length, aspect ratio, density, elasticity, flexibility, and the amount of magnetic material associated with the microposts. In one embodiment, the microposts may include a cylindrical/pillar form factor, a tapered hair-like form factor, a paddle-shaped form factor, or other geometrical forms. In the broadest sense, the micropost structure may be characterized as any structure that includes i) attachment or anchoring to a substrate, ii) responsiveness to an actuating force (e.g., electrical or magnetic actuation force), iii) flexiblity, and iv) a response to the actuation force enabling a method of detection.

There are many possible embodiments that fall within the scope of the present subject matter. The broader inventive concept will now be discussed, as a basis for detailed embodiments to follow. Embodiments of the present subject matter are based on the detection and measurement of light interacting with an active surface (e.g., microposts in a micropost array) on which a specimen of interest (e.g., blood sample) is placed and an actuation force is applied. The detected light amplitude and/or frequency may then be analyzed over a period of time to obtain the desired information about the specimen. Additional methods and means for detection include, but are not limited to, a pickup coil, a Hall sensor, a magneto-resistive sensor, a magnetic sensor, and a capacitive sensor.

Although the present application describes the active surface as a micropost array, other dynamic surfaces may be utilized without departing from the scope of the present subject matter. The term "micropost array" is herein used to describe an array of small, surface attached posts that are anchored and extend outwards from a substrate, that typically range from 1 to 100 micrometers in height. In one embodiment, microposts of a micropost array may be vertically-aligned. Notably, each micropost includes a proximal end that is attached to the substrate base and a distal end or tip that is opposite the proximal end. The substrate base may be partially or entirely transparent as to allow light to pass through. In one embodiment, the micropost array may be situated on a disposable tab that may be inserted into a point of care device.

Materials used to fabricate the micropost array may vary. The micropost array includes at least some elastic material, e.g., an elastomer, or a thin polymer element to allow for the reactive motion of the microposts. The microposts themselves may be entirely or partially made up of an elastomer on either a flexible or non-flexible substrate material. A micropost array as described herein may be considered biomimetic cilia, i.e. an array of silicone-formed structures that resembles biological cilia. In one embodiment, the microposts may comprise of polydimethylsiloxane (PDMS) material. In some embodiments, the micropost material may include any material that is capable of forming to a micro-scale mold. Exemplary) micropost materials include simple polymers, such as Norland Optical Adhesive 81 (NOA81), methacrylate, or perfluoropolyether (PFPE). Other possible materials include a modified PDMS, such as polymerized vinyl-siloxane or thiol-terminated PDMS chains or co-polymers, such as tri-allyl-tri-azine: tetra-thiol-pentacrythritol 2:3. In some embodiments, the micropost material may be cured via a plurality of different curing strategies, such as using a crosslinking catalyst (e.g., Pt) or a photocurable initiator (e.g., TPO-L, BASF, Germany @ 0.1% w/w).

In one embodiment, the elastomer comprising the micropost may include nanoparticles of various materials dispersed throughout, which allows for the fine-tuning of properties of the microposts for particular applications. As used herein, nanoparticles include, but are not limited to metallic, ferromagnetic, or ferroelectric particles. Furthermore, nanoparticles suspended in the micropost material may be non-uniformly distributed throughout the microposts, such that a higher concentration of particles may exist on one side, or end, of the microposts. Alternatively, the microposts may be fabricated to include a piece of a solid material, such as a rod or a shell, which may extend for the full height of a micropost or only a portion of the height of a micropost.

In one embodiment, the top portion of the microposts are coated with a magnetic metal (e.g., via nickel electroplating) which may compel the microposts to deflect in response to a magnetic actuation force. The deflected microposts may then scatter or reflect light emitted from an illumination source. The angles and amplitude in which the reflected and/or scattered light is received at the detection unit may be processed to help determine at least one physical property of a specimen. Specifically, deflection of microposts caused by an actuation force may result in several optical transmission changes (i.e., reflection and/or scattering) in the z-direction. In an alternate embodiment, the microposts may be constructed using an opaque material or coated with an opaque material that is able to scatter or reflect light in some manner.

In some embodiments, a micropost array may be fabricated in such a manner that produces core-shell SAPs. For example, core-shell SAPs may be fabricated by electrodepositing a nickel sulfate solution into a track) etched polycarbonate membrane. In some embodiments, the polycarbonate membrane may be a porous PCTE membrane that is the same thickness as the desired length of the SAPs (e.g., 25 microns). The membrane may be initially sputter-coated with a layer (e.g., 200 nanometers) of metal (e.g., Au or Au/Pd) that acts as a working electrode for the three-electrode electrodeposition cell. After a specified amount of electrical charge (e.g., −50 mC) is applied, the nickel tube-containing membrane (i.e., resulting from the nickel sulfate electrodeposition) can be immersed in uncured liquid PDMS and fixed on a glass coverslip inside a PDMS well (e.g., 250 micrometers tall). Notably, the membrane should be inserted in the PDMS well such that the Au/PD side is facing up. Such an alignment ensures that the nickel tubes encompass the upper portion of the PDMS rod (of a micropost). In some embodiments, the sample may then be cured in an oven at 80 degrees Celsius for at least one hour. After the curing process is completed, the top layer of PDMS and the Au/Pd covering the membrane is removed. The SAPs may then be freed by dissolving the polycarbonate membrane in a solvent (e.g., dichloromethane (DCM)) and rinsing in ethanol and/or water. Alternatively, the ethanol may be replaced/exchanged for any fluid through serial dilutions. In some embodiments, either a coagulation reagent (e.g., kaolin) or calcium chloride for neutralization of citrate anticoagulant may be added to the solution. In addition, the SAP arrays may be subsequently dried (e.g., by lyophilization). In some embodiments, the PDMS well with the fabricated micropost array may be sealed on the top with a glass coverslip.

The term "ferromagnetic" is used herein to refer to any magnetic material, including but not limited to ferromagnetic, diamagnetic, paramagnetic, super-paramagnetic, ferrimagnetic and ferrofluid materials. Likewise, the term "ferroelastomer" is used herein to refer to an elastomer having any type of magnetic nanoparticles dispersed throughout, regardless of how the nanoparticles are bonded to the elastomer, and including but not limited to ferromagnetic, paramagnetic and super-paramagnetic particles. The term "ferroelectric" is used herein to refer to any dielectric material, including but not limited to piezoelectric, pyroelectric, and paraelectric materials.

The material selected for the micropost depends on the intended use of the micropost array, particularly with respect to the actuation method, i.e. the nature of the force to be applied to the microposts. When applying an electrical force (i.e. an electric actuation method), properties of the micropost material to consider include the dielectric constant, polarizability and charge of the material. For a magnetic actuation method, i.e. where a magnetic force is applied, significant properties of the micropost material include permeability and hysteresis.

In one embodiment, the microposts may be chemically treated to achieve a desired surface chemistry that is conducive for testing the specimens. Notably, a reagent may be added to a specimen prior to applying the specimen to the active surface, or the reagent may be pre-applied to the active surface, either as a liquid or solid. The reagent may be applied as a solid by evaporation, lyophilization, or other method of drying. For example, a stable monolayer may be chemically bonded to the microposts during or after the manufacturing process. As another example, a layer of polyethylene glycol (e.g., molecular weight 300) or a lyophilized (e.g., freeze-dried) chemical compound may be applied to the microposts during or after the micropost array has been manufactured. Freeze drying of reagents applied to a micropost array may result (in Phase 2 of the freeze drying process) in collapse of the reagent structure and deposition on the substrate or base to which the microposts are attached and not deposition on the microposts. In one embodiment, determining at least one physical property of a specimen may include the measuring of platelet function (i.e., platelet activation measurement) or the presence or absence of a coagulation factor via the application of a reagent to the specimen that triggers coagulation, restores a coagulation factor, or inhibits a coagulation factor in the specimen. For example, the microposts may be coated with blood coagulation reagents that may affect (e.g., trigger or inhibit) the coagulation of a blood specimen or impact clot lysis (thrombolysis). Alternatively, the reagent may be used to facilitate a factor deficiency test (i.e., to readily identify a specific blood deficiency factor). Similarly, the microposts may be dosed with fluorescent particles that allows the motion of the actuated micropost to be imaged in fluorescence. In one embodiment, a specimen (e.g., a gel specimen) may be designed to change viscosity when combined with (e.g., binds to) another chemical or compound reagent.

As used herein, the term "specimen" may include any analyte, fluid or gel specimen that is biological or synthetic in nature. For example, a specimen may include a synthetic polymer fluid or gel, a biological fluid or gel, or the like. One exemplary specimen includes a biofluid specimen. The term "biofluid" is used herein to refer to any fluid created by the body, including but not limited to whole blood, either oxygenated or deoxygenated, platelet rich plasma, platelet poor plasma, mucus (e.g. sputum, ocular fluid, sinus fluid, and cervical fluid), synovial fluid, pus, and secretions resulting from burns.

Once a specimen is in place, an illumination source may be used to emit light and to be transmitted through the micropost substrate. The emitted light may be detected (and subsequently measured) by a detection unit or system. In one embodiment, the detection system (e.g., detection unit or detection device) may be configured to measure the amplitude of detected light may include, but are not limited to, a photodetection system or a camera. In some embodiments, the detection of emitted light by the detection system is understood to also include the measurement and/or quantification of light amplitude and/or intensity.

In one embodiment, the detection unit/system may utilize an optical, magnetic, or electrical detection means. For example, an optical detection means may include an imaging system, a microscope, a camera system, a photo-detection system, a scattered-light measuring system (e.g., dark field microscopy), a reflected-light measuring system, a transmitted-light measuring system, and a fluorescence measuring system. In some embodiments, optical filters may be utilized by to any of the above mentioned detection unit systems. Optical filters may include, but are not limited to, band-pass optical filters, low-pass optical filters, and high-pass optical filters. In a one embodiment for blood analysis, the light is transmitted off the surface of a reflective substrate, to which the microposts are attached, with said light rays emitted at a predetermined angle less than) 90 degrees from the plane of the substrate and the micropost movement monitored optically at 90 degrees from the plane of the reflective substrate.

The present subject matter further includes an actuation force that is generated in proximity to the active surface which compels at least some of the microposts to exhibit motion. As used herein, the term "actuation force" refers to the drive force applied to the microposts. For example, the actuation force may include a magnetic force or an electrical force. Notably, the actuation force may be applied as a function of frequency and/or amplitude. In one embodiment, the actuation force is applied to compel the microposts to manipulate, mix, or alter the specimen.

In one embodiment, the actuation force causes one or more microposts to deflect/move through the specimen. For example, the actuation force generates a shear force that may activate blood platelets or thrombocytes and subsequently initiate a platelet plug to form in the region of highest shear. Specifically, the actuation force may be used to move the active surface so as to generate sufficient shear to activate platelets in the blood specimen. Although the velocity of the specimen falls to zero near the top and bottom surfaces of the sample chamber/well (e.g., a microfluidic chamber), the portion of the specimen near the moving micropost clings to the micropost and moves at a velocity "V" (e.g., where V is the velocity of motion of the micropost adjacent to a modicum of fluid set into motion). Notably, the shear rate may be defined as the quotient of the micropost velocity and the diameter of the micropost. Thus, the present subject matter allows for large shear rates from modest micropost velocities since the microposts include diameter sizes measured in micrometers. Alternatively, the actuation force may compel the microposts of the active surface to simulate a blood pressure pulse. In one embodiment, a point of care device may be configured to utilize an actuation force to trigger coagulation of a blood specimen in a "shear activation mode" and subsequently switch/revert to a "measurement mode" to monitor the clotting reaction of the specimen. Similarly, the point of care device may also be configured to utilize a "blood pressure pulse" mode to determine if a resulting blood clot can be dislodged.)

In some embodiments, the shear rate needed for a platelet activation measurement may be represented by the following equations:

$$\gamma_{activation} = 2500 \frac{1}{s}$$

$$\eta_{blood}\gamma_{act} = 100 \frac{dyne}{cm^2}$$

where $\gamma_{activation}$ (and $\gamma_{act}$) is the minimum shear rate required to activate platelets, $\eta_{blood}$ is the minimum viscosity of blood, and s is the average center-to-center spacing between microposts.

In some embodiments, a system where the shear rate of the micropost in the measured material is greater or equal to γ activation, the dimensions of the microposts may be represented by the following equation:

$$\frac{3L\sin(\theta)}{\sqrt{2}\, rt} \geq \gamma_{act}$$

wherein L is the length of the microposts, θ is the maximum deflection angle from the vertical axis, r is the radius of the microposts, t is the time in which the micropost reaches angle θ, and $\gamma_{act}$ is the shear rate required for platelet activation.

In some embodiments, a system used for shear activation, there may be additional requirements for the rise time of the magnetic field and the micropost mechanical response time. For example, the system conforms to the following equations:

$$t_{raise} \leq \frac{3L\sin(\theta)}{\sqrt{2}\, r\gamma_{act}}$$

where $t_{raise}$ is the time for the magnetics to reach a maximum magnetic field (see magnetic actuation force and magnetic fields descriptions below for additional context), and:

$$\eta_{blood}\gamma_{act} \leq \frac{9\ln\left(\frac{L}{4r}\right)Er^3\sin(\theta)}{4\sqrt{2}\, L^2 L_{flexible}}$$

where $\eta_{blood}$ is the viscosity of blood, E is the elastic modulus of the flexible region, and $L_{flexible}$ is the length of the flexible region of the micropost.

In one embodiment, platelet shear testing may be conducted using an external pressure source to propel a blood sample or specimen admitted to a first chamber (of a point of care device) through an orifice into a second chamber. The second chamber may include a substrate with microposts driven into motion before or at the time the sample enters the second chamber, thereby enabling the effect of the shear activation of the platelets on the measured variables of a forming blood clot to be determined. In addition, the external pressure source may include a mechanical plunger or a piston applied to the first chamber.

In one embodiment, an actuation unit generates an actuation force that is applied at a fixed amplitude and a fixed frequency over a period of time. By applying the actuation force at a fixed amplitude and fixed frequency, the actuated microposts may deflect in a constant, oscillating manner. When a micropost deflects in response to this type of actuation force, at least a portion of the micropost may occlude at least a portion of the light being emitted by the illumination source. The occlusion caused by the deflection may reduce the amplitude of the light detected by the detection unit (e.g., a photosensor). In another embodiment, the deflecting microposts reflect and/or scatter the light emitted from a light source. In this scenario, a reflected light detection unit or a scattered light detection unit may receive/detect light readings that represent amplitude changes as the microposts are being actuated over a period of time. Regardless of the type of light, data detected or the type of detection unit used, the detection unit passes the amplitude data to the processing unit which then processes the amplitude changes over a period of time and, taking the characteristics of the microposts into account, is able to determine a physical property (e.g., clotting characteristics, such as a clot lysis measurement) of the specimen (e.g., blood sample).

In some embodiments, the microposts may be constructed in a manner such that when deflected, a micropost cannot collapse (e.g., into another micropost to onto the base surface or substrate). In such an embodiment, the microposts may be fabricated to include post dimensions that obey the lesser of the two following equations (i.e., the equation with the smaller calculated product) respectively associated with lateral collapse (i.e., $(L/d)_g$) and ground/substrate collapse (i.e., $(L/d)_g$):

$$\left(\frac{L}{d}\right)_g \leq \frac{\pi^{\frac{5}{3}}}{2^{\frac{11}{3}}3^{\frac{1}{2}}}(1-v^2)^{-\frac{1}{6}}\left(\frac{Ed}{W_g}\right)^{\frac{2}{3}}$$

$$\left(\frac{L}{d}\right)_L \leq \left(\frac{3^3\pi^4}{2^{11}(1-v^2)}\right)^{\frac{1}{12}}\left(\frac{s}{d}\right)^{\frac{1}{2}}\left(\frac{Ed}{W_L}\right)^{\frac{1}{3}}$$

wherein L is the length of the flexible part of the micropost, d is the diameter of the flexible part of the micropost, v is the Poisson ratio of the bending material in the micropost, E is the elastic modulus of the bending material of the micropost, $W_g$ is the maximum energy of adhesion between any part of the micropost and the base surface (or substrate) in the ambient medium, $W_L$ is the maximum energy of adhesion between any part of the microposts in the ambient medium, and s is the average center-to-center spacing between microposts.

The detection system is presented with a signal change, R(a), which is a function of the angle of the micropost deflection, a. For example, to achieve a signal-to-noise ratio of 1, an 8-bit camera with 0.1% noise in the pixel values should see R>1% between upright and deflected microposts. In embodiments that include cylindrical microposts (with hexagonal packing) that are lit in a transmission geometry, the signal change R(a) may be represented as:

$$R(a) > \frac{1-t\frac{4\pi}{3\sqrt{3}}\times\frac{r(\pi r\cos(a)+h\sin(a))}{s^2}}{1-t\frac{4\pi}{3\sqrt{3}}\times\frac{r^2}{s^2}}$$

where, t is the opaqueness ratio, r is the micropost radius, a is the tilt angle (i.e., the micropost deflection angle), h is the height of the microposts, and s is the center-to-center distance to the nearest micropost. This equation is also generalized to approximately describe an optical system where microposts do not exclusively block light (e.g., a scattering-dominated system) by using the opaqueness fraction t to represent the light at the micropost location divided by the background intensity.

The aforementioned signal change equation may also be generalized to approximately describe non-cylindrical posts by replacing the radius r with an effective radius (e.g., $r_{effective}$), such that the area (i.e., $A_{ortho}$) of the orthographic projection of the micropost onto the plane whose normal vector is the illumination axis that is equal to $\pi*r_{effective}^2$.

The above equation may also be generalized to describe non-hexagonally packed micropost arrays and non-cylindrical micropost arrays by replacing the separation s with an average hexagonal separation $s_{avg}$ (shown as s_avg in equation below) such that the fractional occlusion, T, obeys the equation:

$$T = \frac{4\pi}{3\sqrt{3}}\times\frac{r^2}{\text{s\_avg}^2}$$

where T is defined as the fraction of the micropost array's orthographic projection area that is pervaded by the orthographic projections of the micropost array, wherein the projection plane includes a normal vector comprising the illumination axis. In this variation of the equation, r may be replaced with $r_{effective}$ as described above.

In an alternate embodiment, an actuation unit generates an actuation force that is applied at a variable amplitude and a fixed frequency over a period of time. By applying the actuation force at a variable amplitude and) fixed frequency, the actuated microposts may deflect in a variable oscillating manner. As the actuation force is applied with a variable amplitude, a fixed duty cycle, and a fixed frequency, the processing unit also receives feedback information pertaining to the varying actuation force amplitude. The varying actuation force amplitude feedback data is then used with the received light data (i.e., transmitted, scattered, and/or reflected light detected by the detection unit) at the processing unit to adjust the actuation force amplitude. For example, using the feedback data, the processing unit may modulate the amplitude of the actuation force in a manner that maintains a fixed duty cycle and a fixed amplitude for the detected light (i.e., the signal received by the detection unit is at a fixed amplitude). By processing the actuation force amplitude changes over a period of time (which is received as feedback) and taking the characteristics of the microposts into account, the processing is able to determine a physical property (e.g., clotting characteristics) of the specimen (e.g., blood sample).

In a third embodiment, the present subject matter may employ pulse width modulation (PWM). For example, an actuation unit may generate an actuation force that is applied at a fixed amplitude, a variable duty cycle, and a variable frequency over a period of time such that the signal received by the detection unit is at a fixed amplitude. In this scenario, the processing unit receives the frequency of the actuation force as feedback data. The varying actuation force frequency feedback data is then used with the received light data (i.e., transmitted, scattered, and/or reflected light detected by the detection unit) at the processing unit to adjust the actuation force frequency. For example, using the feedback data, the processing unit may modulate the frequency of the actuation force in a manner that maintains a fixed amplitude for the detected light (i.e., the signal received by the detection unit is at a fixed amplitude). By processing the actuation force frequency changes over a period of time (which is received as feedback) and taking the characteristics of the microposts into account, the processing is able to determine a physical property (e.g., clotting characteristics, such as a clot lysis measurement) of the specimen (e.g., blood sample).

For example, an actuation force with a fixed amplitude may be applied to the microposts such that the microposts are deflected to a certain point. The present subject matter may then be configured to modulate either the actuation force and/or the amplitude of the detected light in order to continuously deflect one or more microposts to a certain deflection point each time the actuation force is applied. In such an embodiment, the detection unit may include a motion sensing/capturing mechanism, such as an imaging system or a camera.

In one embodiment, the point of care device may be configured to provide a plurality of the actuation force modes disclosed above. In such an embodiment, the point of care device may be adapted to select and/or switch among the plurality of actuation force modes. The point of care device may be activated to initially function in a "manipulation mode" or a "mixing mode" and subsequently switched to a "measurement mode" or a "feedback mode" to optimize data quality. For example, an initial actuation force mode may perturbs a specimen and a subsequent mode measures the effect of that perturbation, or where the subsequent mode is used to optimize the quality of the detection method. In one embodiment, an actuation force mode may be switched to or from at least one detection method mode that measures the effect of a manipulation mode or optimizes the quality of the method by using another detection mode.

After the amplitude of the detected light has been measured, the measurement data are provided by the detection unit to a processing unit that processes the data in order to determine at least one property of the specimen based on the detected light and the predefined characteristics of the microposts. For example, as a blood specimen begins to clot, the motion of the microposts becomes restricted, and the measured amplitude of light detected by the photosensor increases since it becomes more difficult for the microposts to deflect in the clotting blood. Thus, the emitted light is less likely to be occluded by the deflected (i.e., bent over) microposts. The resulting amplitude measurements provided to the processing unit may be utilized to determine a physical property of the specimen. Exemplary properties of a specimen that may be measured by the present subject matter include clotting properties, coagulation properties, thrombolysis properties, rheological properties, and other physical properties.

In one embodiment, the processing unit may be configured to use existing clot measurement assays, including, but not limited to, PT and INR determination, PTT, APPT, and other blood coagulation tests, to determine clotting characteristics of a specimen (i.e., blood). The processing unit may also or alternatively be configured to determine the clot strength, known rheologically as stiffness, of a forming thrombus or the breakdown time of a blood clot, known as fibrinolysis (i.e. the foregoing determinations could be made via measurements over a period of time). Clotting strength and/or stiffness is an important measure for the prediction and treatment of severe bleeding in a surgical setting or some other scenario involving physical trauma. Notably, the surface attached micropost arrays utilized in the present subject matter enable clot strength tests to be performed by a portable POC device in the field in trauma cases. This is a novel application, since there is currently no readily available point of care system for use in the field in trauma cases.

Reference will now be made in detail to exemplary embodiments of the present subject matter, examples of which are illustrated in the accompanying drawings. Wherever possible, the same reference numbers will be used throughout the drawings to refer to the same or like parts.

In one embodiment, the present subject matter includes a standalone device that is configured to test physical properties of a specimen. One such embodiment of a standalone device for testing properties of a specimen includes a point of care (POC) device. For example, FIG. 1 is a block diagram illustrating an exemplary point of care system according to an embodiment of the subject matter described herein. In one embodiment, the present subject matter may be implemented as a point of care system within a portable device for field use. FIG. 1 depicts a portable POC device 100 that includes an actuation unit 102, a detection unit 104 (e.g., a photosensor, a photodetector, phototransistor, etc.), a processing unit 106 (e.g., a microcontroller processor), an illumination or light source 108 (e.g., an LED light or near infrared light source) and a memory unit 110. In one embodiment, memory unit 110 may be configured to store measurement readings processed/recorded by processing unit 106. Memory unit 110 may also be configured to store a software and/or firmware application that facilitates the measurement of detected light and is executed by processing unit 106.

Figure 2:
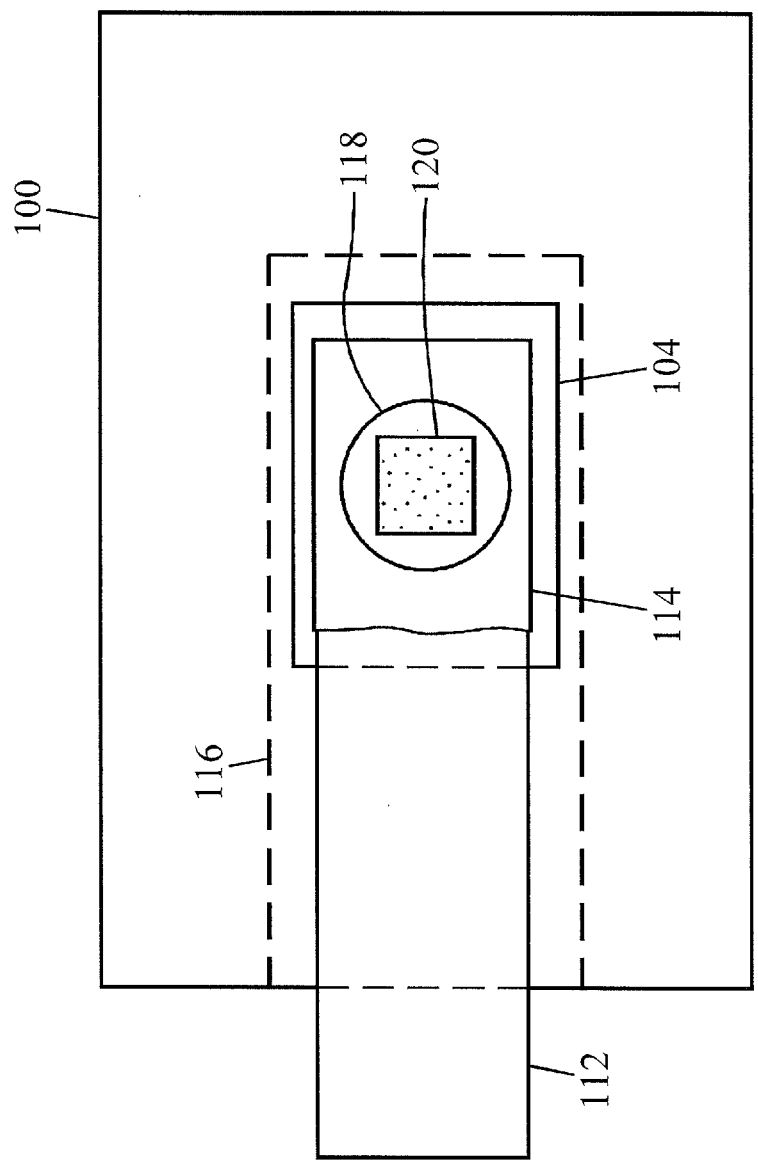
FIG. 2 is a block diagram depicting a top view of a portable point of care diagnostic device for determining

Device 100 may further include an ingress port 116, which is adapted to receive an inserted disposable tab 112. Tab 112 may include an end portion 114, which comprises an active surface such as micropost array 120 (as shown in FIG. 2). The end portion 114 is configured to receive a small sample size of a specimen (e.g., blood, mucus, synovial fluid, etc.). The surface attached microposts, or cilia, as described above, may include silicone-based pillars or microposts, some of which may contain a ferromagnetic material at the distal end (i.e., the end that is not attached to the substrate base). In one embodiment, the microposts may be vertically-aligned posts that are attached and anchored to a substrate. The microposts may also be stamped with a substance such as fibronectin, an extracellular matrix protein, to attract cells when placed on micropost tips. In one embodiment, tab 112 may be inserted in port 116 such that end portion 114 containing the specimen is close enough to actuation unit 102 for a actuation force (e.g., a magnetic force) generated by actuation unit 102 to effect movement (i.e., compel motion and/or deflection) of the microposts.

In one embodiment, actuation unit 102 includes a low-power system (i.e., which may be electrically powered by either a small battery or manual actuation produced by a small hand-crank). For example, actuation unit 102 may include a small spinning permanent magnet adapted to generate a time varying magnetic field. Device 100 may be controlled by a user to apply the magnetic field to end portion 114 of tab 112, thereby causing a deflection motion (e.g., oscillation) of microposts on the end portion 114. For example, processing unit 106 may be configured to activate and deactivate actuation unit 102, thereby turning the generated magnetic field on and off. When the magnetic field is turned on, the microposts in micropost array portion 120 are compelled to bend or deflect toward the horizontal plane. When the magnetic field is turned off, the microposts in micropost array portion 120 return to the original upright position. In some embodiments, the magnetic field needed to compel either a paramagnetic micropost or superparamagnetic micropost to deflect can include a magnetic field direction that is between the micropost's tilt angle, a, and 90°. In contrast, the magnetic field direction may be between a and 180° for a ferromagnetic post.

In the event the microposts are deflected toward the horizontal plane, the microposts are positioned to occlude or block the light emitted from light source 108 from being detected by detection unit 104.

As the microposts are compelled to move and deflect by actuation unit 102, detection unit 104 may measure and record the amplitude of detected light (i.e., light emitted from light source 108) interacting with the active surface, such as the microposts on end portion 114. In one embodiment, detection unit 104 may include a photosensor, photodetection system, a scattered-light measuring system, a reflected-light measuring system, a transmitted-light measuring system, or any like device/system that is configured to detect amplitude or frequency changes in emitted light. For example, in one embodiment, detection unit 104 is configured to detect the light emitted from an illumination source and traversing through the substrate. As the microposts are actuated and deflect, the emitted light may be occluded and detection unit 104 detects the resulting change in the light amplitude or frequency (e.g., color, wavelength, etc.). In some embodiments, the wavelength of light used in the detection of the post actuation may be selected based on its ability to transmit through the specimen or material under study. For example, the absorption of oxygenated blood reaches a minimum level at a wavelength of 690 nanometers, while deoxygenated blood decreases steadily at illumination wavelengths greater than 600 nanometers. In some embodiments, the absorption spectra cross or intersect at approximately 780 nanometers. If the light to be detected is found to at or near this wavelength, then the optical properties of the specimen will have a reduced sensitivity to whether the blood is oxygenated or deoxygenated.)

In an alternate embodiment, detection unit 104 may be configured to detect the light emitted from an illumination source that is reflected or scattered off of the microposts. The measured light frequency or amplitude of detected light by detection unit 104 may also change based on the degree in which the microposts are deflected by the actuation force.

The data obtained by detection unit 104 may be forwarded to processing unit 106 for calculations and analysis. Alternatively, device 100 may be provisioned with a radio uplink (not shown) to wirelessly provide the data to a processing unit on a separate computer. The calculations and analysis performed by the processing unit may include determining a measure of biofluid rheology based on the force applied by actuation system 102 and the resulting light amplitude detected by detection unit 104. Processing unit 104 may also be configured to take into account the characteristics/properties of the microposts to determine a physical property of a specimen being tested. For example, properties that of the microposts that may be considered by processing unit 104 may include the diameter, length, aspect ratio, flexibility, density, and elasticity of the microposts. In addition, the amount of magnetic material included in the microposts may also be taken into account. In one embodiment, the characteristics and properties of the microposts are stored in memory unit 110 for use by processing unit 104.

In one embodiment, processing unit 104 may also be configured to generate results not unlike a classical thromboelastography (TEG) test, such as a reaction time value (i.e., R value), a K value, an angle value, and a maximum amplitude value. For example, the reaction time value represents the amount of time elapsed when the first clot is detected and the K value is a value that represents the speed of clot formation, e.g., the time from when the first clot is detected to the time it takes until the clot reaches a designated measurement (e.g., 20 mm). The angle value represents the tangent of the curve made as the K value is reached and the maximum amplitude is an indication of clot strength. In an alternative embodiment, processing unit 104 may also be configured to generate results similar to a rotational thromboelastometry (ROTEM) test, such as the reaction time, clotting time (CT), clot formation time (CFT), maximal clot firmness (MCF), maximum lysis, and the like. Notably, processing unit 104 may be configured to generate results substantially identical to those of any type of clotting time test, platelet activation measurement test (i.e., a platelet function test), glucose test, or the like.

In some embodiments, a glucose test may be utilized where a reagent applied to the microposts would be a material whose elastic or viscous properties change in the presence of glucose. This may be a polymer gel that reacts in a reversible or irreversible manner with the glucose (or other analyte) level in the blood, so as to alter the viscoelasticity of the gel that surrounds the posts. This material and the posts would reside in one chamber of the test strip, enclosed by a semipermeable membrane. On the other side of this membrane would be a parallel channel in which the blood to be analyzed may flow. The glucose concentration (or other analyte concentration) in the blood would come to equilibrium, through the semipermeable membrane, with the concentration of analyte in the gel/post chamber. The motion of the posts would then measure the elastic or viscous properties of the reagent which would be calibrated for varying levels of glucose (or other analyte), and the corresponding micropost motion in the reagent would be analyzed to determine the concentration of glucose (or other analyte) in the specimen.

In some embodiments, physical property measurements are conducted at a constant temperature (e.g., 37 degrees Celsius). Temperature control may ensure repeatable the viscoelastic properties of the specimen and microposts, as well as ensure repeatable chemical reactivity within the specimen, or between the specimen and the microposts.

FIG. 2 is a block diagram depicting a top view of POC device 100 which illustrates disposable tab 112 inserted in port 116. Notably, FIG. 2 illustrates disposable tab 112 as including a distal tip portion 114 that includes a sample well 118 (e.g., a microfluidic chamber) that contains an active surface, i.e., a micropost array portion 120, that is used to receive and hold a specimen, such as a blood specimen. In one embodiment, disposable tab 112 may be embodied a microfluidic test strip configured to contain and test blood from a finger pricking. In one embodiment, micropost array portion 120 may include an area of flexible microposts anchored to a transparent or translucent substrate section that permits light emitted from light source 108 to traverse through micropost array portion 120 and be received by detection unit 104.

Figure 3:
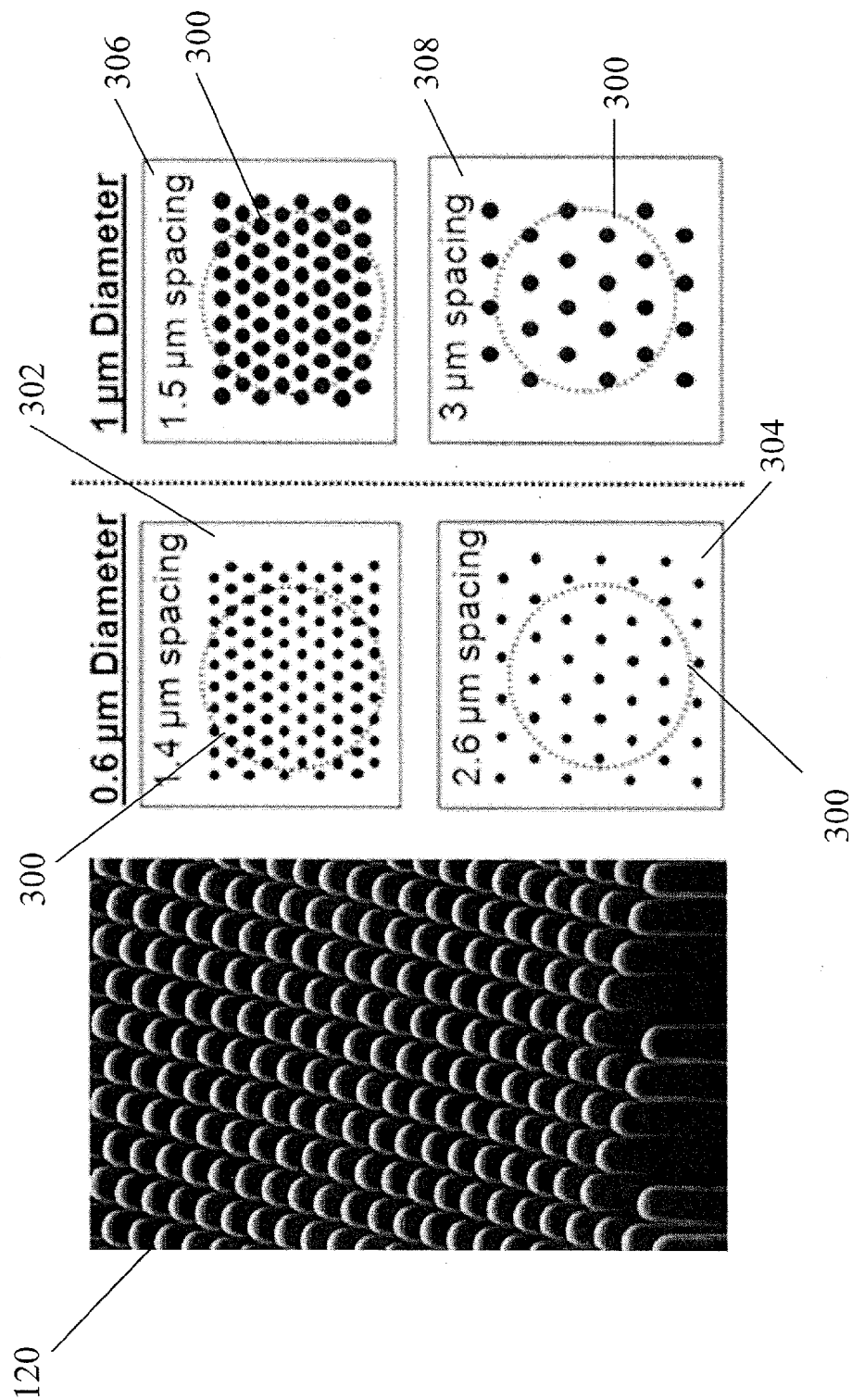
FIG. 3 is a diagram of an exemplary micropost array according to an embodiment of the subject matter described herein.

FIG. 3 is a diagram of an exemplary micropost array according to an embodiment of the subject matter described herein. A scanning electron microscope image of a micropost array 120 is shown. FIG. 3 also depicts possible size and spacing variations for the microposts of micropost array 120 that may be positioned in a sample well 300 (e.g., not unlike well 118 depicted in FIG. 2) of a disposable tab. In one embodiment, sample well 300 includes a microfluidic chamber. FIG. 3 also depicts that the microposts of an array may vary in size and in proximity with each other on an array. For example, box 302 illustrates microposts that are 0.6 micrometers in diameter and positioned 1.4 micrometers apart from one another. Likewise, box 304 illustrates microposts that are also 0.6 micrometers in diameter, but are spaced 2.6 micrometers apart. Box 306 illustrates microposts of 1 micrometer in diameter that are spaced 1.5 micrometers apart, while box 308 illustrates microposts of 1 micrometer in diameter spaced 3 micrometers apart. It is understood that the size and dimensions depicted in FIG. 3 are for exemplary purposes and do not limit the scope of the present subject matter.

Figure 4:
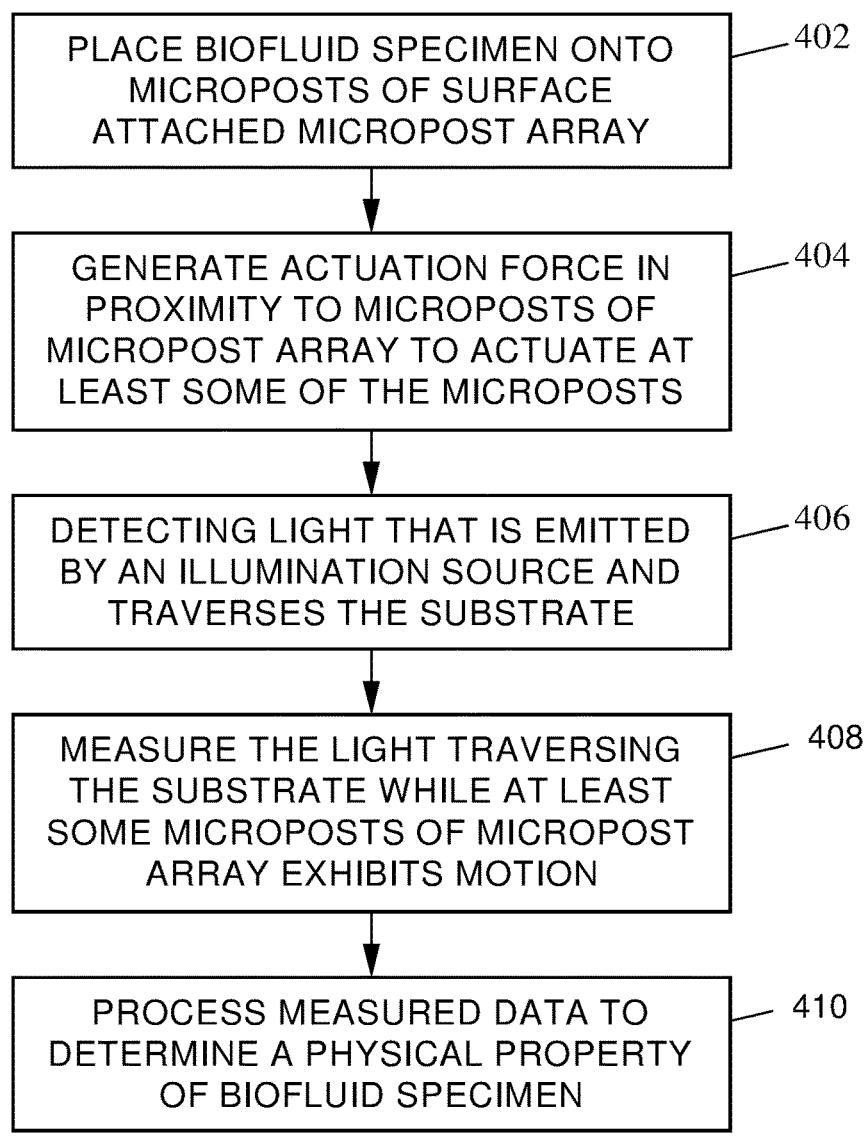
FIG. 4 is a flow chart illustrating an exemplary process for determining physical properties of a specimen in a portable point of care diagnostic device according to an embodiment of the subject matter described herein.

FIG. 4 is a flow chart illustrating an exemplary process 400 for determining a physical property of a specimen using a portable POC device according to an embodiment of the subject matter described herein. Referring to FIG. 4, in block 402, a specimen is placed on microposts of an active surface, such as a surface attached micropost array, such as, for example, the microposts in well 118 of a disposable tab, wherein the well contains at least a portion of micropost array 120 (e.g., see FIG. 2). In block 404, an actuation force is generated in proximity to the microposts. In one embodiment, a magnetic actuator (e.g., actuator 102 in FIG. 1) applies a magnetic force via the magnetic field and/or its gradient to the microposts) located in the well in order to move the microposts with the applied specimen.

In block 406, light that is emitted by an illumination source is detected. In one embodiment, an illumination source 108 emits light that traverses through the substrate of the micropost array and is detected by detection unit 104. Notably, the microposts are being compelled to move by the magnetic actuator thereby causing the microposts to occlude the amount of light that is able to be detected by detection unit 104. As the microposts are deflected, the amplitude of the light detected varies. In an alternate embodiment, a detection unit 104 may be configured to detect light that is reflected or scattered off of the actuated microposts.

In block 408, the light interacting with the active surface is measured. In one embodiment, the amplitude of the detected light is measured as the microposts are being deflected by the actuation force. For example, the amplitude data may be sent to processing unit 106, which is configured to process the data to derive measurement data.

In block 410, the measured data is processed to determine at least one of a physical property of the specimen. In one embodiment, the physical property of the specimen includes a rheological measurement of a natural fluid, a natural gel, a synthetic fluid, or a synthetic gel. For example, the specimen may include a material whose rheological property is modified by the environment and where the rheological measurement constitutes a measurement of that environmental variable, where that environmental variable may include the pH, the temperature, the concentration of chemical species, the concentration of biochemical species, the concentration of virus, bacteria, pathogen, parasite, the concentration of an antibody, the concentration of glucose, the concentration of a drug, or the concentration dissolved gas. In one embodiment, the determination of at least one physical property of the specimen includes conducting a clot lysis measurement on the specimen.

For example, processing unit may be configured to process the measurement data to determine the physical properties of the specimen. In one embodiment, processing unit 106 may take into account the characteristics of the microposts (e.g., length, density, etc.) and the amplitude of the detected light over a period of time in order to derive clotting properties of a blood specimen. Exemplary properties that may be measured include blood clotting, blood coagulation, and blood thrombolysis.

In some embodiments, the present subject matter includes a system for testing a physical property of a specimen that includes an active surface configured to receive a specimen and that includes a plurality of microposts extending outwards from a substrate, wherein each micropost includes a proximal end attached to the substrate and a distal end opposite the proximal end. The system further includes an actuation unit configured to generate an actuation force in proximity to the micropost array that compels at least some of the microposts to exhibit motion. The system may also include a detection unit configured to detect light that is emitted by an illumination source and interacts with the active surface while the at least some microposts exhibit motion in response to the actuation force. The system further includes a processing unit configured to measure data (e.g., enabling the acquisition of data) that represents the detected light interacting with the active surface, and to determine at least one physical property of the specimen based on the measured (e.g., acquired) data.

In some embodiments of the above system, the microposts are configured in which each of the microposts do not collapse either onto another of the microposts or onto the substrate.

In some embodiments of the above system, each of the microposts is configured with dimensions that comply with the lesser of:

$$\left(\frac{L}{d}\right)_g \leq \frac{\pi^{\frac{5}{3}}}{2^{\frac{11}{3}}3^{\frac{1}{2}}}(1-v^2)^{-\frac{1}{6}}\left(\frac{Ed}{W_g}\right)^{\frac{2}{3}}$$

$$\left(\frac{L}{d}\right)_L \leq \left(\frac{3^3\pi^4}{2^{11}(1-v^2)}\right)^{\frac{1}{12}}\left(\frac{s}{d}\right)^{\frac{1}{2}}\left(\frac{Ed}{W_L}\right)^{\frac{1}{3}}$$

wherein L is a bending length of the micropost, d is a bending diameter of the micropost, v is a Poisson ratio of bending material in the micropost, E is) an elastic modulus of the bending material of the micropost, $W_g$ is the maximum energy of adhesion between any part of the micropost and the substrate, $W_L$ is a maximum energy of the adhesion between any part of the micropost in the ambient medium, and s is an average center-to-center spacing between each of the plurality of microposts.

In some embodiments of the above system, the detection unit may be further configured to detect a signal change that is a function of a deflection angle of the microposts.

In some embodiments of the above system, the deflection angle of the micropost is a and the detected signal change is represented by R(a).

In some embodiments of the above system, the detected signal change is greater than:

$$\frac{1-t\frac{4\pi}{3\sqrt{3}}\times\frac{r(\pi r\cos(a)+h\sin(a))}{s^2}}{1-t\frac{4\pi}{3\sqrt{3}}\times\frac{r^2}{s^2}}$$

where t is an opaqueness ratio of each of the plurality of microposts, r is a radius of each of the plurality of microposts, h is a height of the plurality of microposts, and s is the average center-to-center distance spacing between each of the plurality of microposts.

In some embodiments of the above system, the actuation force includes a magnetic force that comprises a magnetic field direction between a and 90 degrees, wherein the each of the microposts comprise either a paramagnetic micropost or a superparamagnetic micropost.

In some embodiments of the above system, the actuation force includes a magnetic force that comprises a magnetic field direction between a and 180 degrees, wherein the each of the microposts comprise a ferromagnetic micropost.

In some embodiments of the above system, determining at least one physical property of the specimen includes performing a platelet activation measurement that includes a shear rate is less than or equal to:

$$\frac{3L\sin(\theta)}{\sqrt{2}\,rt}$$

wherein dimensions of each of the microposts comprise L as a length of the microposts, θ as a maximum deflection angle from the vertical axis, r as a radius of each of the microposts, t as a time in which each of the microposts reaches the angle θ.

In some embodiments of the above system, the microposts are fabricated by immersing a polycarbonate membrane into liquid polydimethylsiloxane (PDMS) contained in a PDMS well, wherein the polycarbonate membrane is previously subjected to an electrodeposition of a nickel based solution.

In some embodiments of the above system, the microposts are fabricated by curing the PDMS surrounding the membrane in the PDMS well and subsequently dissolving the polycarbonate membrane such that the microposts and the substrate remain in the PDMS well.

In some embodiments of the above system, the at least one physical property of the specimen includes a clot lysis measurement of a blood specimen.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method comprising:
   receiving, by a portable point of care device, a specimen applied to an active surface that includes a micropost array comprising a plurality of microposts extending outwards from a substrate, wherein each micropost includes a proximal end attached to the substrate and a distal end opposite the proximal end, and a metallic, ferromagnetic or ferroelectric material on at least a portion of some of the microposts;
   generating, by the portable point of care device, an actuation force in proximity to the micropost array that compels at least some of the microposts to exhibit motion, wherein the actuation force is applied in accordance with a varying actuation force amplitude or a varying actuation force frequency;
   detecting light that is emitted by an illumination source within the portable point of care device and that interacts with the active surface while the at least some microposts exhibit motion in response to the actuation force;
   measuring data that represents the detected light interacting with the active surface; and
   determining at least one physical property of the specimen based on the measured data and feedback data pertaining to either the varying actuation force amplitude or the varying actuation force frequency, wherein the feedback data is used to adjust the amplitude or frequency of the actuation force.

2. The method of claim 1 wherein a reagent is added to the specimen prior to applying the specimen to the active surface or the reagent is pre-applied to the active surface as a liquid or solid.

3. The method of claim 1 wherein the specimen comprises blood and the physical property comprises a clotting property, a lysis property, a platelet function property, or a clot stiffness property of the blood.

4. The method of claim 1 wherein the actuation force comprises an electric or magnetic force.

5. The method of claim 1 wherein the actuation force is applied to the at least some of the microposts to manipulate, mix, or alter the specimen.

6. The method of claim 1 wherein the generated actuation force is able to be switched from among a plurality of different actuation force modes, including one or more of a manipulation mode, a measurement mode, a mixing mode, and a detection method mode.

7. A system comprising:
   an active surface configured to receive a specimen and that includes a micropost array comprising a plurality of microposts extending outwards from a substrate, wherein each micropost includes a proximal end attached to the substrate, a distal end opposite the proximal end, and a metallic, ferromagnetic or ferroelectric material on at least a portion of some of the microposts;
   an actuation unit in a portable point of care device configured to generate an actuation force in proximity to the micropost array that compels at least some of the microposts to exhibit motion when the active surface is received by the portable point of care device, wherein the actuation force is applied in accordance with a varying actuation force amplitude or a varying actuation force frequency;
   an illumination source in the portable point of care device configured to emit light;
   a detection unit in the portable point of care device configured to detect the light that is emitted by the illumination source and interacts with the active surface while the at least some microposts exhibit motion in response to the actuation force; and
   a processing unit in the portable point of care device configured to measure data that represents the detected light interacting with the active surface and to determine at least one physical property of the specimen based on the measured data and feedback data pertaining to either the varying actuation force amplitude or the varying actuation force frequency, wherein the feedback data is used to adjust the amplitude or frequency of the actuation force.

8. The system of claim 7 wherein a reagent is added to the specimen prior to the active surface receiving the specimen or the reagent is pre-applied to the active surface as a liquid or solid.

9. The system of claim 7 wherein the specimen comprises blood and the physical property comprises a clotting property, a lysis property, a platelet function property, or a clot stiffness property of the blood.

10. The system of claim 7 wherein the actuation force comprises an electric or magnetic force.

11. The system of claim 7 wherein the actuation force is applied to the at least some of the microposts to manipulate, mix, or alter the specimen.

12. The system of claim 7 wherein the generated actuation force is able to be switched from among a plurality of different actuation force modes, including at least one of a manipulation mode, a measurement mode, a mixing mode, and a detection method mode.

* * * * *